United States Patent
Zhang et al.

(10) Patent No.: US 12,071,387 B2
(45) Date of Patent: Aug. 27, 2024

(54) THERMAL COUPLING METHOD FOR PREPARING ETHYLENE BY ETHANOL DEHYDRATION AND DEVICE THEREOF

(71) Applicant: TIANJIN UNIVERSITY, Tianjin (CN)

(72) Inventors: Minhua Zhang, Tianjin (CN); Hao Gong, Tianjin (CN); He Dong, Tianjin (CN); Feng Shi, Tianjin (CN); Fang Meng, Tianjin (CN); Yingzhe Yu, Tianjin (CN); Haoxi Jiang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 18/211,391

(22) Filed: Jun. 19, 2023

(65) Prior Publication Data
US 2024/0067583 A1 Feb. 29, 2024

(30) Foreign Application Priority Data
Aug. 30, 2022 (CN) .......................... 202211056719.8

(51) Int. Cl.
*C07C 1/24* (2006.01)
*C07C 7/04* (2006.01)
*C07C 7/12* (2006.01)
*C09K 5/04* (2006.01)

(52) U.S. Cl.
CPC .................. *C07C 1/24* (2013.01); *C07C 7/04* (2013.01); *C09K 5/042* (2013.01); *C07C 7/12* (2013.01); *C09K 2205/12* (2013.01)

(58) Field of Classification Search
CPC .... C07C 1/24; C07C 7/04; C07C 7/12; C09K 5/042; C09K 2205/12
See application file for complete search history.

(56) References Cited

U.S. PATENT DOCUMENTS

2015/0368215 A1* 12/2015 Coupard .............. C07D 301/03
549/534
2015/0376151 A1* 12/2015 Coupard ................... C07C 1/24
549/523

FOREIGN PATENT DOCUMENTS

CN 113045372 A 6/2021

OTHER PUBLICATIONS

Translation of CN113045372A. (Year: 2021).*

* cited by examiner

*Primary Examiner* — Ali Z Fadhel

(57) ABSTRACT

The present disclosure relates to a thermal coupling method for preparing ethylene by ethanol dehydration and device thereof. The device includes an ethanol dehydration reaction system, a quenching compression system, an alkaline washing system, a molecular sieve drying system and an ethylene purification and propylene refrigeration cycle system; ethanol dehydration reaction products in the ethanol dehydration reaction system serve as a heat source for preheating, vaporization and superheating of a raw material of ethanol; tower bottoms of an evaporation tower in the quenching compression system serve as a heat source for preheating of a feed stream of the evaporation tower and heating of an overhead gas of a quenching tower; products of ethylene in the alkaline washing system serve as a cold source for cooling of crude ethylene.

4 Claims, 4 Drawing Sheets

THERMAL COUPLING METHOD FOR PREPARING ETHYLENE BY ETHANOL DEHYDRATION AND DEVICE THEREOF

CROSS-REFERENCE TO RELATED APPLICATION

This application claims priority from the Chinese patent application 2022110567198 filed Aug. 30, 2022, the content of which is incorporated herein in the entirety by reference.

TECHNICAL FIELD

The present disclosure belongs to the field of ethylene synthesis and refining, and relates to a thermal coupling method and device for preparing ethylene by ethanol dehydration, which reduces energy consumption.

BACKGROUND ART

Ethylene is the most important organic chemical raw material, and its industrial scale, yield and technical level are important symbols for the development of the national chemical industry. Throughout the world, ethylene raw materials in industrialized countries are mainly light raw materials. Ethylene produced with naphtha as a cracking raw material accounts for about 50% of the total ethylene yield in the world. Ethane is the second largest cracking raw material, and ethylene produced by cracking of the ethane accounts for about 28% of the total ethylene yield in the world. The ethylene produced by cracking of the above two raw materials goes beyond 75% of the total ethylene yield, and the rest of ethylene is mainly prepared from liquefied petroleum gas (LPG), condensate oil, middle distillate and the like as raw materials.

The preparation of ethylene from ethanol is achieved by ethanol dehydration under the action of catalysts at appropriate temperature, and the preparation of ethylene by catalytic dehydration of ethanol is the earliest technological method used to produce ethylene in industry. Unlike the production of ethylene by petrochemical raw materials, the raw material for the preparation of ethylene from ethanol is ethanol, which can be obtained by fermentation of biomass. Biomass is characterized by renewability, low pollution and wide distribution. Important biomass capable of supplying energy includes wood, wood wastes, crops, wastes generated during food processing, aquatic plants and the like. The process route of the preparation of ethylene from biomass ethanol also has the advantages of short construction period, relatively less investment, mild production conditions and the like; and in the preparation of ethylene by this production process, $CO_2$ emissions are reduced, and products have high purity and simple compositions, so that they are relatively easy to separate and purify.

Production of ethylene by dehydration of ethanol produced with renewable biomass raw materials is one of important ways to adjust energy structure, reduce environmental pollution and promote sustainable development of national economy and society. For the preparation of ethylene by ethanol dehydration, the current main research focuses on improving the technological process, reducing the material and energy consumption of devices and increasing benefits.

In the existing literature or patents, there were few special reports on comprehensive utilization of energy. CN103121898A provided a refrigerating fluid system arranged between first and second ethylene coolers and an ethylene de-light component tower reboiler, and material heat at an outlet of an ethylene compressor serves as a heat source of the ethylene de-light component tower reboiler to reduce energy consumption. However, in the whole process of preparing ethylene by ethanol dehydration, the energy consumption of the ethylene de-light component tower accounts for a very small proportion in the total energy consumption. The energy saving effect obtained by arranging a refrigerant system is very limited. CN106608787A provided an optimization of a heat exchanger network, and the raw material of ethanol and fed process water were heated by high-temperature reaction products. However, this method is only limited to the utilization of heat from the preparation of ethylene by ethanol reaction, without considering supplementation and utilization of heat throughout the process. Therefore, the heat utilization of the whole technological process should be considered comprehensively, to really achieve the purposes of reducing energy consumption and saving the operating cost.

SUMMARY

The objective of the present disclosure is to provide a thermal coupling energy integrated production device and a corresponding method thereof. The method is applied to the ethylene preparation by ethanol dehydration. According to the method, heat exchange in the system is rationally disposed to reduce energy consumption greatly on the premise of obtaining high-purity ethylene.

In order to realize the above objective of the present disclosure, the technical scheme of the present disclosure is as follows:

A thermal coupling method for preparing ethylene by ethanol dehydration is provided, includes an ethanol dehydration reaction system, a quenching compression system, an alkaline washing system, a molecular sieve drying system and an ethylene purification and propylene refrigeration cycle system; wherein ethanol dehydration reaction products in the ethanol dehydration reaction system serve as a heat source for preheating, vaporization and superheating of a raw material of ethanol; tower kettle fluid of an evaporation tower in the quenching compression system serve as a heat source for preheating of a feed stream of the evaporation tower and heating of an overhead gas of a quenching tower; products of ethylene in the alkaline washing system serve as a cold source for cooling of crude ethylene; tower kettle fluid of the evaporation tower in the molecular sieve drying system serve as a heat source for preheating of circulating ethylene; the products of ethylene in the ethylene purification and propylene refrigeration cycle system serve as a cold source for precooling of dried ethylene; the circulating ethylene serves as a cold source for cooling of an overhead gas of a demethanizing tower and cooling of propylene; low-temperature propylene serves as a cold source for cooling of an overhead gas of a purification tower and further cooling of the ethylene; and hot propylene serves as a heat source for heating of the tower bottoms of the demethanizing tower, the tower bottoms of the purification tower and the products of ethylene.

The ethanol dehydration reaction system includes an ethanol preheater, ethanol evaporators, an ethanol evaporation tank, an ethanol superheater, a first gas-liquid separation tank, a third reactor and a heating furnace; the quenching compression system includes an evaporation tower, an evaporation tower feed preheater, an evaporation tower reboiler, a quenching tower, a quenching tower overhead gas heater, a second gas-liquid separation tank, an evaporatower bottom cooler and a process water tank; the ethanol dehydration reaction products enter the ethanol superheater to superheat ethanol steam; the cooled reaction products enter the ethanol evaporators to vaporize the liquid phase raw material of ethylene, and then the reaction products enter the ethanol preheater to preheat the liquid phase raw material of ethylene; the ethanol dehydration reaction products cooled repeatedly are fed into the first gas-liquid separation tank; the tower bottoms of the evaporation tower enter the evaporation tower feed preheater to preheat the feed stream of the evaporation tower, the cooled tower bottoms of the evaporation tower enter the quenching tower overhead gas heater to heat the overhead gas of the quenching tower, and then the tower bottoms of the evaporation tower are fed into the process water tank; and the evaporation tower reboiler condensates are fed into the molecular sieve drying system.

The alkaline washing system includes an alkaline washing tower, a crude ethylene cooler and a third gas-liquid separation tank; the molecular sieve drying system includes drying towers, a circulating ethylene preheater and a steam condensate flash tank; the products of ethylene from the ethylene purification and propylene refrigeration cycle system enter the crude ethylene cooler to cool crude ethylene produced in the alkaline washing tower, and then the products of ethylene are fed into a product ethylene heater; and the evaporation tower reboiler condensates from the quenching compression system enter the circulating ethylene preheater to preheat the circulating ethylene, and the cooled reboiler condensates are fed into the steam condensate flash tank.

The ethylene purification and propylene refrigeration cycle system includes an ethylene precooler, an ethylene chiller, a demethanizing tower, a demethanizing tower condenser, a demethanizing tower reboiler, a purification tower, a purification tower condenser, a purification tower reboiler, an ethylene reflux tank, a propylene cooler, a fuel gas tank, a product ethylene heater, a primary propylene flash tank, a propylene collection tank, and a secondary propylene compressor; the circulating ethylene enters the demethanizing tower condenser to cool the overhead gas of the demethanizing tower, the heated circulating ethylene is fed into the propylene cooler to cool propylene, and then the circulating ethylene is fed into the molecular sieve drying system; the products of ethylene enter the ethylene precooler to cool the dried crude ethylene, and the heated products of ethylene are fed into the alkaline washing system, and then discharged out of a boundary region after being heated; the low-temperature propylene enters the purification tower condenser to cool the overhead gas of the purification tower, the heated low-temperature propylene is fed into the ethylene chiller to further cool the ethylene, and then the low-temperature propylene is fed into the primary propylene flash tank; and hot propylene from the outside of the boundary region enters the demethanizing tower reboiler, the purification tower reboiler and the product ethylene heater respectively to heat the tower bottoms of the demethanizing tower, the tower bottoms of the purification tower and the products of ethylene, and the cooled propylene is fed into the propylene collection tank.

According to the device of the thermal coupling method for preparing ethylene by ethanol dehydration in the present disclosure, in the ethanol dehydration reaction system, a tube pass inlet of the ethanol preheater is connected with a raw material tank area; a shell pass inlet of the ethanol preheater is connected with a shell pass outlet of the ethanol evaporator; a tube pass outlet of the ethanol preheater is connected with an inlet of the ethanol evaporation tank; a shell pass outlet of the ethanol preheater is connected with an inlet of the first gas-liquid separation tank; a tube pass inlet of the ethanol evaporator is connected with an outlet in a bottom of the ethanol evaporation tank; a shell pass inlet of the ethanol evaporator is connected with a shell pass outlet of the ethanol superheater; a tube pass outlet of the ethanol evaporator is connected with an inlet in a right side of the ethanol evaporation tank; a tube pass inlet of the ethanol superheater is connected with an outlet at a top of the ethanol evaporation tank; a shell pass inlet of the ethanol superheater is connected with an outlet of the third reactor; a tube pass outlet of the ethanol superheater is connected with an inlet of the heating furnace; in the quenching compression system, an outlet of the tower kettle of the evaporation tower is connected with a shell pass inlet of the evaporation tower feed preheater; an outlet of the tower kettle of the quenching tower is connected with a tube pass inlet of the evaporation tower feed preheater; a tube pass outlet of the evaporation tower feed preheater is connected with an inlet at a top of the evaporation tower; a shell pass outlet of the evaporation tower feed preheater is connected with a shell pass inlet of the quenching tower overhead gas heater; an overhead steam outlet of the quenching tower is connected with a tube pass inlet of the quenching tower overhead gas heater; a tube pass outlet of the quenching tower overhead gas heater is connected with an inlet of the second gas-liquid separation tank; and a shell pass outlet of the quenching tower overhead gas heater is connected with an inlet of the evaporation tower bottom cooler.

According to the device of the thermal coupling method for preparing ethylene by ethanol dehydration in the present disclosure, in the alkaline washing system, an overhead steam outlet of the alkaline washing tower is connected with a shell pass inlet of the crude ethylene cooler; a tube pass outlet of the ethylene precooler is connected with a tube pass inlet of the crude ethylene cooler; a shell pass outlet of the crude ethylene cooler is connected with an inlet of the third gas-liquid separation tank; a tube pass outlet of the crude ethylene cooler is connected with a tube pass inlet of the product ethylene heater; in the molecular sieve drying system, a shell pass inlet of the circulating ethylene preheater is connected with a shell pass outlet of the evaporation tower reboiler; a tube pass inlet of the circulating ethylene preheater is connected with a tube pass outlet of the propylene cooler; a tube pass outlet of the circulating ethylene preheater is connected with inlets of the drying towers; and a shell pass outlet of the circulating ethylene preheater is connected with an inlet of the steam condensate flash tank.

According to the device of the thermal coupling method for preparing ethylene by ethanol dehydration in the present disclosure, in the ethylene purification and propylene refrigeration cycle system, a shell pass inlet of the ethylene precooler is connected with outlets of the drying towers; a tube pass inlet of the ethylene precooler is connected with an outlet of the ethylene buffer tank; a shell pass outlet of the ethylene precooler is connected with a shell pass inlet of the ethylene chiller; a tube pass inlet of the ethylene chiller is connected with an outlet of the secondary propylene compressor; a tube pass outlet of the ethylene chiller is connected with an inlet of a primary propylene separation tank; a shell pass outlet of the ethylene chiller is connected with an inlet of the demethanizing tower; an overhead steam outlet of the demethanizing tower is connected with a shell pass inlet of the demethanizing tower condenser; a tube pass inlet of the demethanizing tower condenser is connected with an outlet of the ethylene reflux tank; a tube pass outlet of the demethanizing tower condenser is connected with a tube pass inlet of the propylene cooler; a shell pass outlet of the demethanizing tower condenser is connected with an inlet of the fuel gas tank; an outlet of the tower kettle of the demethanizing tower is connected with a tube pass inlet of the demethanizing tower reboiler; a tube pass outlet of the demethanizing tower reboiler is connected with an inlet of the tower kettle of the demethanizing tower; a shell pass outlet of the demethanizing tower reboiler is connected with an inlet of the propylene collection tank; an overhead steam outlet of the purification tower is connected with a shell pass inlet of the purification tower condenser; a tube pass inlet of the purification tower condenser is connected with an outlet of the secondary propylene compressor; a shell pass outlet of the purification tower condenser is connected with an inlet of the ethylene reflux tank; a tube pass outlet of the purification tower condenser is connected with an inlet of the primary propylene flash tank; an outlet of the tower kettle of the purification tower is connected with a tube pass inlet of the purification tower reboiler; a tube pass outlet of the purification tower reboiler is connected with an inlet of the tower kettle of the purification tower; a shell pass outlet of the purification tower reboiler is connected with an inlet in a top of the propylene collection tank; a shell pass inlet of the propylene cooler is connected with an outlet at bottom of the propylene collection tank; a shell pass outlet of the propylene cooler is connected with an inlet of the primary propylene flash tank; and a shell pass outlet of the product ethylene heater is connected with an inlet at top of the ethylene collection tank.

Heat exchangers in the present disclosure are all shell and tube heat exchangers.

According to the device for achieving the thermal coupling method for preparing ethylene by ethanol dehydration in the present disclosure, in the ethanol dehydration reaction system, the tube pass inlet of the ethanol preheater is connected with the raw material tank area; the shell pass inlet of the ethanol preheater is connected with the shell pass outlet of the ethanol evaporator; the tube pass outlet of the ethanol preheater is connected with the inlet of the ethanol evaporation tank; the shell pass outlet of the ethanol preheater is connected with the inlet of the first gas-liquid separation tank; the tube pass inlet of the ethanol evaporator is connected with the outlet in at the bottom of the ethanol evaporation tank; the shell pass inlet of the ethanol evaporator is connected with the shell pass outlet of the ethanol superheater; the tube pass outlet of the ethanol evaporator is connected with the inlet in the right side of the ethanol evaporation tank; the tube pass inlet of the ethanol superheater is connected with the outlet in the at top of the ethanol evaporation tank; the shell pass inlet of the ethanol superheater is connected with the outlet of the third reactor; and the tube pass outlet of the ethanol superheater is connected with the inlet of the heating furnace. In the quenching compression system, the outlet of the tower kettle of the evaporation tower is connected with the shell pass inlet of the evaporation tower feed preheater; the outlet of the tower kettle of the quenching tower is connected with the tube pass inlet of the evaporation tower feed preheater; the tube pass outlet of the evaporation tower feed preheater is connected with the inlet at the top of the evaporation tower; the shell pass outlet of the evaporation tower feed preheater is connected with the shell pass inlet of the quenching tower overhead gas heater; the overhead steam outlet of the quenching tower is connected with the tube pass inlet of the quenching tower overhead gas heater; the tube pass outlet of the quenching tower overhead gas heater is connected with the inlet of the second gas-liquid separation tank; and the shell pass outlet of the quenching tower overhead gas heater is connected with the inlet of the evaporation tower bottom cooler. In the alkaline washing system, the overhead steam outlet of the alkaline washing tower is connected with the shell pass inlet of the crude ethylene cooler; the tube pass outlet of the ethylene precooler is connected with the tube pass inlet of the crude ethylene cooler; the shell pass outlet of the crude ethylene cooler is connected with the inlet of the third gas-liquid separation tank; the tube pass outlet of the crude ethylene cooler is connected with the tube pass inlet of the product ethylene heater; in the molecular sieve drying system, the shell pass inlet of the circulating ethylene preheater is connected with the shell pass outlet of the evaporation tower reboiler; the tube pass inlet of the circulating ethylene preheater is connected with the tube pass outlet of the propylene cooler; the tube pass outlet of the circulating ethylene preheater is connected with the inlets of the drying towers; and the shell pass outlet of the circulating ethylene preheater is connected with the inlet of the steam condensate flash tank; in the ethylene purification and propylene refrigeration cycle system, the shell pass inlet of the ethylene precooler is connected with the outlets of the drying towers; the tube pass inlet of the ethylene precooler is connected with the outlet of the ethylene buffer tank; the shell pass outlet of the ethylene precooler is connected with the shell pass inlet of the ethylene chiller; the tube pass inlet of the ethylene chiller is connected with the outlet of the secondary propylene compressor; the tube pass outlet of the ethylene chiller is connected with the inlet of the primary propylene separation tank; the shell pass outlet of the ethylene chiller is connected with the inlet of the demethanizing tower; the overhead steam outlet of the demethanizing tower is connected with the shell pass inlet of the demethanizing tower condenser; the tube pass inlet of the demethanizing tower condenser is connected with the outlet of the ethylene reflux tank; the tube pass outlet of the demethanizing tower condenser is connected with the tube pass inlet of the propylene cooler; the shell pass outlet of the demethanizing tower condenser is connected with the inlet of the fuel gas tank; the outlet of the tower kettle of the demethanizing tower is connected with the tube pass inlet of the demethanizing tower reboiler; the tube pass outlet of the demethanizing tower reboiler is connected with the inlet of the tower kettle of the demethanizing tower; the shell pass outlet of the demethanizing tower reboiler is connected with the inlet of the propylene collection tank; the overhead steam outlet of the purification tower is connected with the shell pass inlet of the purification tower condenser; the tube pass inlet of the purification tower condenser is connected with the outlet of the secondary propylene compressor; the shell pass outlet of the purification tower condenser is connected with the inlet of the ethylene reflux tank; the tube pass outlet of the purification tower condenser is connected with the inlet of the primary propylene flash tank; the outlet of the tower kettle of the purification tower is connected with the tube pass inlet of the purification tower reboiler; the tube pass outlet of the purification tower reboiler is connected with the inlet of the tower kettle of the purification tower; the shell pass outlet of the purification tower reboiler is connected with the inlet in the top of the propylene collection tank; the shell pass inlet of the propylene cooler is connected with the outlet in the bottom of the propylene collection tank; the shell pass outlet of the propylene cooler is connected with the inlet of the primary propylene flash tank; and the shell pass outlet of the product ethylene heater is connected with the inlet in the top of the ethylene collection tank.

The specific description with reference to the drawings is given as follows:

Ethanol in the raw material tank area enters the ethanol preheater 101 to be heated, then enters the ethanol evaporation tank 102, and is heated to be evaporated in the ethanol evaporators 108, 109. Ethanol steam evaporated from the ethanol evaporation tank 102 is fed into the reactor for a reaction after being heated by the ethanol superheater 103. A high-temperature reaction gas from the third reactor 107 enters the first gas-liquid separation tank 110 after superheating the ethanol steam, vaporizing the liquid phase raw material of ethanol and preheating the liquid phase raw material of ethanol in sequence, and then the gas is fed into the quenching compression system after gas-liquid separation.

After a gas phase of the first gas-liquid separation tank, a gas phase of a degassing tank and a gas exhausted from the drying towers enter the quenching tower 113, an overhead gas of the quenching tower enters the second gas-liquid separation tank 123 after being heated. Tower kettle fluid of the quenching tower are fed into the evaporation tower feed preheater 117 to be heated, and then enter the evaporation tower 119. After heating the feed stream of the evaporation tower and the overhead gas of the quenching tower in sequence, tower bottoms in the evaporation tower enter the process water tank 122 after being cooled by the evaporation tower bottom cooler 121.

A gas exhausted from the second gas-liquid separation tank 123 enters the alkaline washing tower 126 after being compressed and cooled, and a gas exhausted from the top of the tower enters the third gas-liquid separation tank 129 after being cooled by the products of ethylene through the crude ethylene cooler 128. A gas phase separated from the third gas-liquid separation tank 129 is fed into the drying towers to be dehydrated, and the dried ethylene after dehydration is fed into the ethylene purification and propylene refrigeration cycle system.

Dried crude ethylene from the molecular sieve drying system is fed into the ethylene chiller 144 to be recooled after being cooled by the ethylene precooler 142, and then enters the demethanizing tower 145. The overhead gas of the demethanizing tower is fed into the fuel gas tank 156 after being cooled in the demethanizing tower condenser 147. Ethylene produced from the tower kettle is fed into the purification tower 149, and the products of ethylene produced from the top of the purification tower enter the ethylene reflux tank 152 after being cooled in the purification tower condenser 151. A part of products of ethylene serving as circulating ethylene, are used as a cold source of the demethanizing tower condenser 147 and the ethylene cooler 155, and then are fed into the drying towers to serve as a desorbed gas. The rest products of ethylene are fed into an ethylene buffer tank 153. Part of ethylene in the ethylene buffer tank 153 is fed back to the top of the purification tower as reflux, and after recycling of cold energy from the rest of ethylene by the ethylene precooler 142 and the crude ethylene cooler 128, the rest of ethylene is discharged out of the boundary region as the products of ethylene after being heated by hot propylene through the product ethylene heater 157.

The present disclosure has the following advantages and beneficial effects:

In the present disclosure, through optimization of the heat exchanger network, heat exchange of the ethanol dehydration reaction products with the raw materials of ethanol is conducted for three times, and therefore each stream of heat from high-temperature ethanol reaction products is fully utilized. The tower bottoms of the evaporation tower serve as a heat exchange medium for the evaporation tower feed preheater and the quenching tower overhead gas heater for heat recycling. The cold energy of the products of ethylene is recycled by the ethylene precooler and the crude ethylene cooler, and hot propylene is introduced as a heating stream, thereby avoiding cooling of the hot propylene with cooling water and fully achieving internal cycling of the propylene to reduce introduction of external heating steam. Through heat exchange among different materials, heat exchange in the system is disposed rationally to reduce the usage amount of a utility medium in the process of preparing ethylene by ethanol dehydration. The energy consumption is reduced by about 48% on the premise of meeting the separation requirements. Under the same production task, each stream of heat is fully utilized in the present disclosure, and the heat exchange in the system is disposed rationally to reduce the energy consumption greatly, decrease the equipment investments significantly, and reduce the ethylene production cost.

DETAILED DESCRIPTION OF THE PRESENT DISCLOSURE

Figure 1:
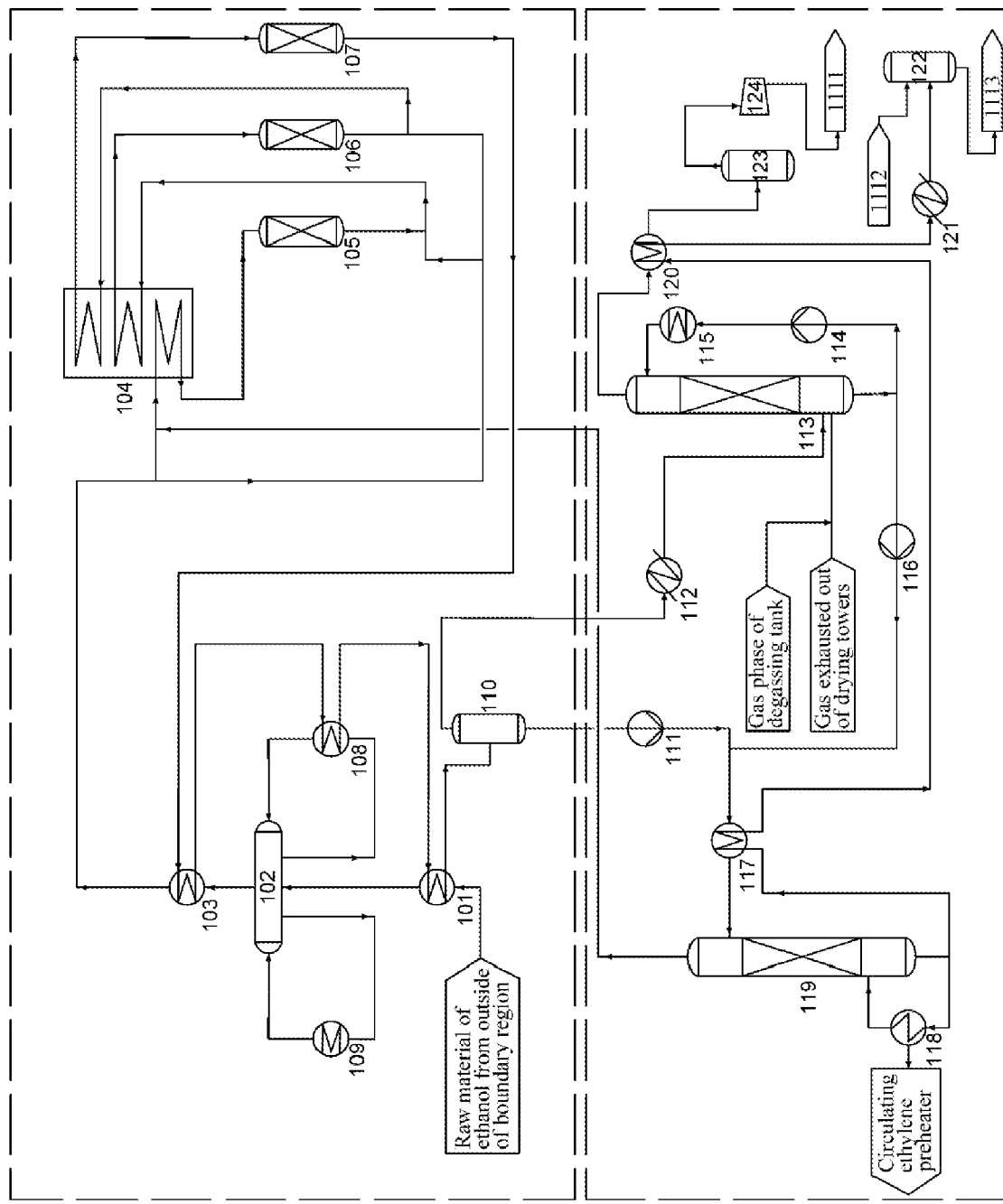
FIG. 1 is a flow diagram of an ethanol dehydration system and a quenching compression system in a thermal coupling method of a process for preparing ethylene by ethanol dehydration.
Figure 2:
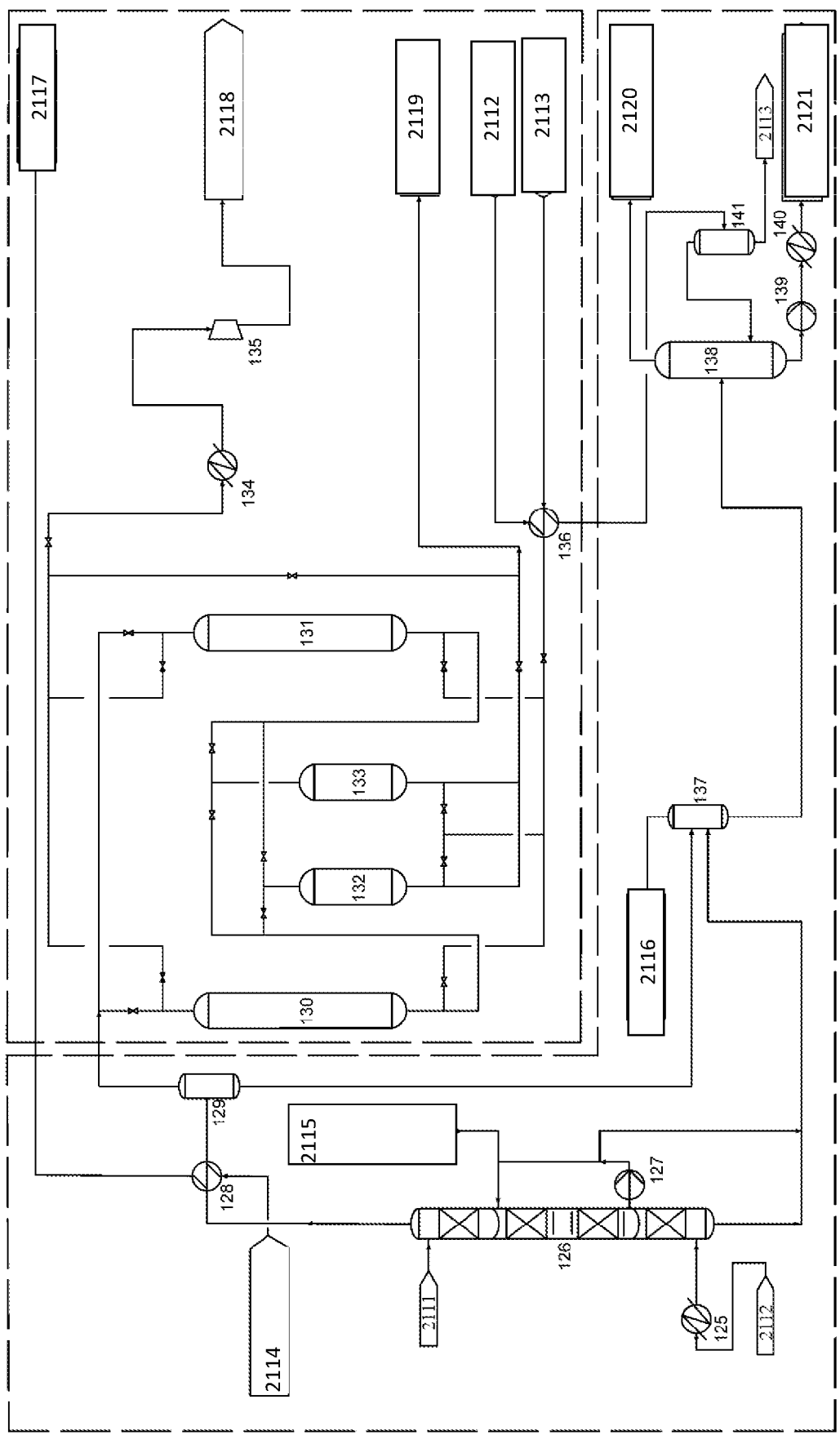
FIG. 2 is a flow diagram of an alkaline washing system and a molecular sieve drying system in a thermal coupling method of a process for preparing ethylene by ethanol dehydration.
Figure 3:
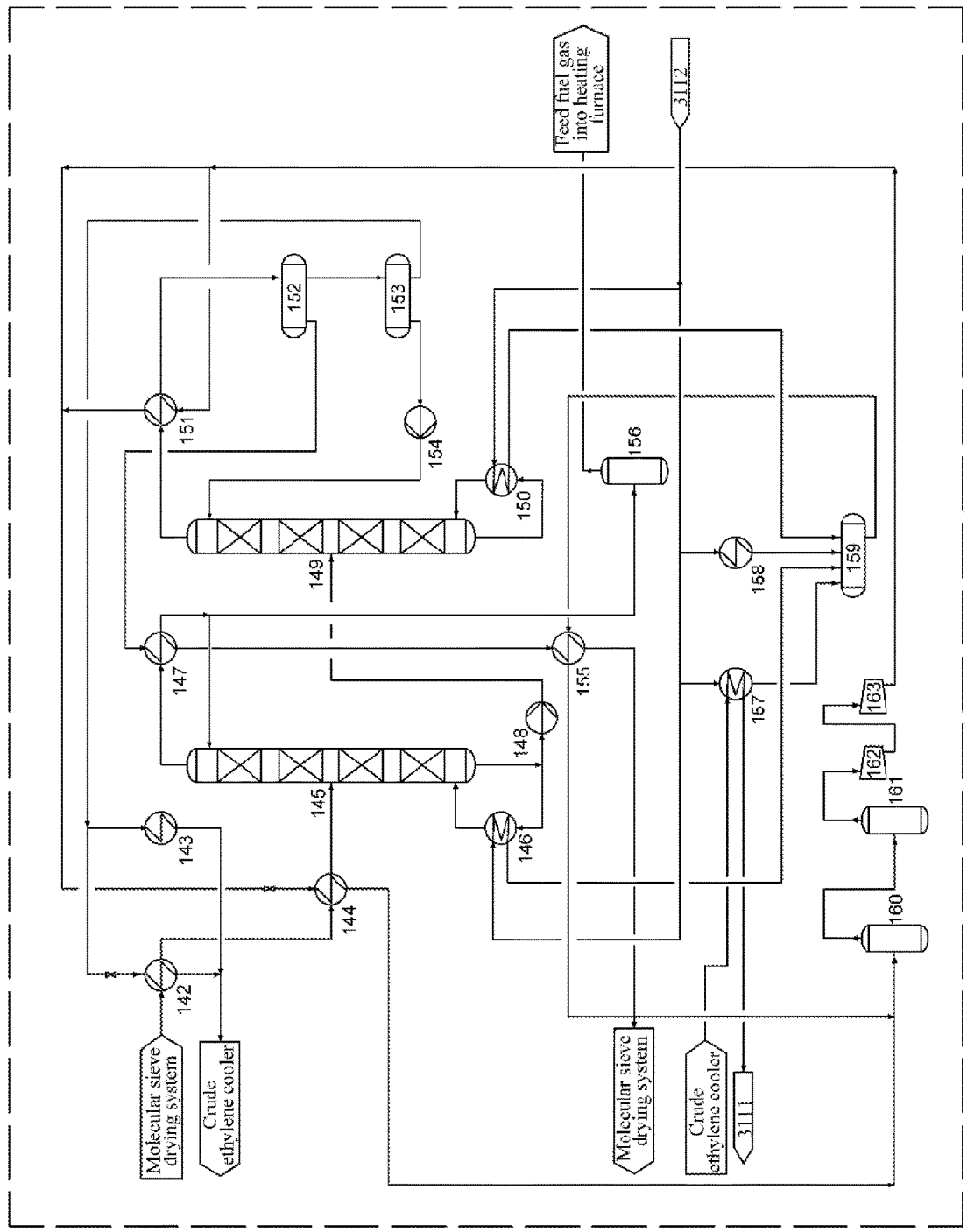
FIG. 3 is a flow diagram of an ethylene purification and propylene refrigeration cycle system in a thermal coupling method of a process for preparing ethylene by ethanol dehydration.
Figure 4:
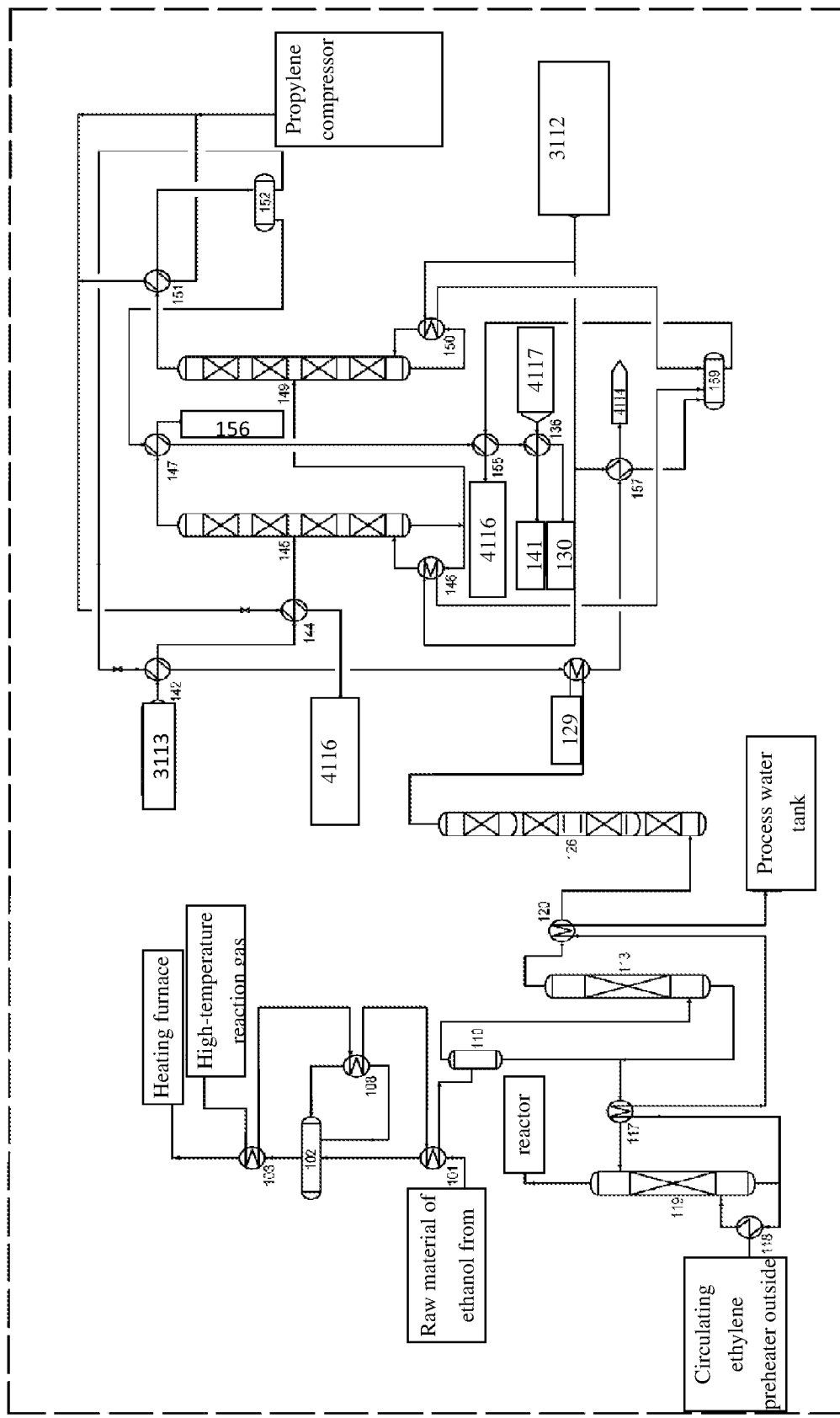
FIG. 4 is a schematic diagram of a whole process in a thermal coupling method of a process for preparing ethylene by ethanol dehydration.

The present disclosure will be further described in detail below with reference to FIGS. 1, 2, 3, and 4 and specific embodiments. The following embodiments are merely descriptive and not restrictive, and should not be construed as limiting the protection scope of the present disclosure.

In the figures, the following reference characters represent the corresponding features: 1111: feed phase ethylene into alkaline washing system; 1112: desalted water from outside of boundary region; 1113: feed process water into alkaline washing system; 2111: process water of quenching compression system; 2112: crude ethylene of quenching compression system; 2113: drain row-pressure condensates out of boundary region; 3111: discharge products of ethylene out of boundary region; 3112: gas phase polypropylene from outside of boundary region; 4112: steam condensate flash tank; and 4114: discharge products of ethylene out of boundary; 2114: ethylene of ethylene evaporator; 2115: fresh alkaline liquid; 2116: feed into quenching tower; 2117: ethylene product heater; 2118: feed exhausted gas into quenching tower; 2119: ethylene purification system; 2120: exhaust waste gas out of boundary region; 2121: drain waste liquor out of boundary region; 3113: molecular sieve drying system; 3115: feed fuel gas into heating furnace; 4116: primary propylene flash tank; 4117: evaporation tower reboiler.

According to a device for achieving a thermal coupling method for preparing ethylene by ethanol dehydration in the present disclosure, in an ethanol dehydration reaction system, a tube pass inlet of an ethanol preheater is connected with a raw material tank area; a shell pass inlet of the ethanol preheater is connected with a shell pass outlet of an ethanol evaporator; a tube pass outlet of the ethanol preheater is connected with an inlet of an ethanol evaporation tank; a shell pass outlet of the ethanol preheater is connected with an inlet of a first gas-liquid separation tank; a tube pass inlet of the ethanol evaporator is connected with an outlet in a at bottom of the ethanol evaporation tank; a shell pass inlet of the ethanol evaporator is connected with a shell pass outlet of an ethanol superheater; a tube pass outlet of the ethanol evaporator is connected with an inlet in a right side of the ethanol evaporation tank; a tube pass inlet of the ethanol superheater is connected with an outlet in at a top of the ethanol evaporation tank; a shell pass inlet of the ethanol superheater is connected with an outlet of a third reactor; and a tube pass outlet of the ethanol superheater is connected with an inlet of a heating furnace. In a quenching compression system, an outlet of a tower kettle of an evaporation tower is connected with a shell pass inlet of an evaporation tower feed preheater; an outlet of a tower kettle of a quenching tower is connected with a tube pass inlet of the evaporation tower feed preheater; a tube pass outlet of the evaporation tower feed preheater is connected with an inlet in at a top of the evaporation tower; a shell pass outlet of the evaporation tower feed preheater is connected with a shell pass inlet of a quenching tower overhead gas heater; an overhead steam outlet of the quenching tower is connected with a tube pass inlet of the quenching tower overhead gas heater; a tube pass outlet of the quenching tower overhead gas heater is connected with an inlet of a second gas-liquid separation tank; and a shell pass outlet of the quenching tower overhead gas heater is connected with an inlet of an evaporation tower bottom cooler. In an alkaline washing system, an overhead steam outlet of an alkaline washing tower is connected with a shell pass inlet of a crude ethylene cooler; a tube pass outlet of an ethylene precooler is connected with a tube pass inlet of the crude ethylene cooler; a shell pass outlet of the crude ethylene cooler is connected with an inlet of a third gas-liquid separation tank; a tube pass outlet of the crude ethylene cooler is connected with a tube pass inlet of a product ethylene heater; in a molecular sieve drying system, a shell pass inlet of a circulating ethylene preheater is connected with a shell pass outlet of an evaporation tower reboiler; a tube pass inlet of the circulating ethylene preheater is connected with a tube pass outlet of a propylene cooler; a tube pass outlet of the circulating ethylene preheater is connected with inlets of drying towers; a shell pass outlet of the circulating ethylene preheater is connected with an inlet of a steam condensate flash tank; in an ethylene purification and propylene refrigeration cycle system, a shell pass inlet of an ethylene precooler is connected with outlets of the drying towers; a tube pass inlet of the ethylene precooler is connected with an outlet of an ethylene buffer tank; a shell pass outlet of the ethylene precooler is connected with a shell pass inlet of an ethylene chiller; a tube pass inlet of the ethylene chiller is connected with an outlet of a secondary propylene compressor; a tube pass outlet of the ethylene chiller is connected with an inlet of a primary propylene separation tank; a shell pass outlet of the ethylene chiller is connected with an inlet of a demethanizing tower; an overhead steam outlet of the demethanizing tower is connected with a shell pass inlet of a demethanizing tower condenser; a tube pass inlet of the demethanizing tower condenser is connected with an outlet of an ethylene reflux tank; a tube pass outlet of the demethanizing tower condenser is connected with a tube pass inlet of a propylene cooler; a shell pass outlet of the demethanizing tower condenser is connected with an inlet of a fuel gas tank; an outlet of a tower kettle of the demethanizing tower is connected with a tube pass inlet of a demethanizing tower reboiler; a tube pass outlet of the demethanizing tower reboiler is connected with an inlet of the tower kettle of the demethanizing tower; a shell pass outlet of the demethanizing tower reboiler is connected with an inlet of a propylene collection tank; an overhead steam outlet of a purification tower is connected with a shell pass inlet of a purification tower condenser; a tube pass inlet of the purification tower condenser is connected with an outlet of a secondary propylene compressor; a shell pass outlet of the purification tower condenser is connected with an inlet of the ethylene reflux tank; a tube pass outlet of the purification tower condenser is connected with an inlet of a primary propylene flash tank; an outlet of the tower kettle of the purification tower is connected with a tube pass inlet of the purification tower reboiler; a tube pass outlet of the purification tower reboiler is connected with an inlet of the tower kettle of the purification tower; a shell pass outlet of the purification tower reboiler is connected with an inlet at a top of the propylene collection tank; a shell pass inlet of the propylene cooler is connected with an outlet at a bottom of the propylene collection tank; a shell pass outlet of the propylene cooler is connected with an inlet of the primary propylene flash tank; and a shell pass outlet of a product ethylene heater is connected with an inlet in a top of the ethylene collection tank.

The present disclosure provides a production process for preparing ethylene by ethanol dehydration, and the specific implementation is as follows:

Ethanol in a raw material tank area enters an ethanol preheater 101 to be heated to 135° C.-140° C. by a high-temperature dehydration reaction gas, then enters an ethanol evaporation tank 102, and is heated to be evaporated in ethanol evaporators 108, 109. A heating medium in the ethanol evaporator 108 is the high-temperature dehydration reaction gas. Ethanol steam evaporated from the ethanol evaporation tank 102 is divided into three streams to be fed into a reactor for a reaction after being heated to 324° C.-327° C. by the high-temperature dehydration reaction gas through an ethanol superheater 103. A high-temperature reaction gas from a third reactor 107 enters a first gas-liquid separation tank 110 after its heat is recovered by the ethanol superheater 103, the ethanol evaporator 108 and the ethanol preheater 101 in sequence. A separated liquid phase therefrom is fed into an evaporation tower 119 by a separation tank discharge pump 111, and a gas phase is fed into a quenching tower 113 after being cooled.

After a gas phase of the first gas-liquid separation tank, a gas phase of a degassing tank and a gas exhausted from drying towers enter the quenching tower 113, an overhead gas of the quenching tower enters a second gas-liquid separation tank 123 after being heated by tower bottoms of the evaporation tower through a quenching tower overhead gas heater 120. The tower bottoms of the quenching tower are fed into an evaporation tower feed preheater 117 to be heated to 110° C.-114° C. by the tower bottoms of the evaporation tower, and then enter the evaporation tower 119. Steam produced from the top of the evaporation tower returns to a dehydration reaction section as diluted steam. After heat of the tower bottoms in the evaporation tower are recovered by the evaporation tower feed preheater 117 and the quenching tower overhead gas heater 120, the tower bottoms enter a process water tank 122 after being cooled by an evaporation tower bottom cooler 121.

A gas exhausted from the second gas-liquid separation tank 123 enters an alkaline washing tower 126 after being compressed and cooled, and a gas exhausted from the top of the tower enters a third gas-liquid separation tank 129 after being cooled to 18° C.-22° C. by low-temperature products of ethylene through a crude ethylene cooler 128. A gas phase separated from the third gas-liquid separation tank 129 is fed into the drying towers to be dehydrated, and the dried ethylene after dehydration is fed into a demethanizing tower 145 and a purification tower 149 to be refined at low temperature.

Dried crude ethylene from the molecular sieve drying system is fed into an ethylene chiller 144 to be recooled by low-temperature propylene after being cooled to −32° C. to −28° C. by the liquid phase products of ethylene through an ethylene precooler 142, and then enters the demethanizing tower 145 after being cooled to −40° C. to −35° C. The overhead gas of the demethanizing tower is fed into a heating furnace 104 as a fuel gas after being cooled to −68° C. to −64° C. by decompressed circulating ethylene in a demethanizing tower condenser 147 and vaporized in a fuel gas tank 156. Ethylene produced in the tower kettle is fed into a purification tower 149, and the products of ethylene produced from the top of the purification tower enter an ethylene reflux tank 152 after being cooled to −36° C. to −34° C. by low-temperature propylene through a purification tower condenser 151. A part of products of ethylene, serving as the circulating ethylene, are used as a cold source of the demethanizing tower condenser 147 and a propylene cooler 155, and then are fed into the drying towers to serve as a desorbed gas. The rest products of ethylene are fed into an ethylene buffer tank 153. Part of ethylene in the ethylene buffer tank is fed back to the top of the purification tower as reflux, and after cold energy is recycled from the rest of ethylene by the ethylene precooler 142 and the crude ethylene cooler 128, the rest of ethylene is discharged out of the boundary region as the products of ethylene after being heated to 23° C.-26° C. by hot propylene through a product ethylene heater 157. A demethanizing tower reboiler 146 and a purification tower reboiler 150 are heated by the hot propylene, and resulting propylene condensates are fed into a propylene collection tank 159.

The device involved in the above technical scheme includes an ethanol preheater 101, an ethanol superheater 103, a heating furnace 104, a third reactor 107, an ethanol evaporator 108, a first gas-liquid separation tank 110, an evaporation tower feed preheater 112, a quenching tower 113, an evaporation tower 119, a quenching tower overhead gas heater 120, an evaporation tower bottom cooler 121, a process water tank 122, a second gas-liquid separation tank 123, an alkaline washing tower 126, a crude ethylene cooler 128, a third gas-liquid separation tank 129, drying towers 130-133, a circulating ethylene preheater 136, a steam condensate flash tank 141, an ethylene precooler 142, an ethylene chiller 144, a demethanizing tower 145, a demethanizing tower reboiler 146, a demethanizing tower condenser 147, a purification tower 149, a purification tower reboiler 150, a purification tower condenser 151, an ethylene reflux tank 153, a propylene cooler 155, a fuel gas tank 156, a product ethylene heater 157, a propylene collection tank 159, a primary propylene flash tank 160, and a secondary propylene compressor 163.

The specific implementation process of the method of the present disclosure is described with the specific embodiments below.

Embodiment 1

Ethanol in a raw material tank area enters an ethanol preheater 101 to be heated to 135° C. by a high temperature dehydration reaction gas, then enters an ethanol evaporation tank 102, and is heated to be evaporated in ethanol evaporators 108, 109. A heating medium in the ethanol evaporator 108 is the high temperature dehydration reaction gas. Ethanol steam evaporated from the ethanol evaporation tank 102 is divided into three streams to be fed into the reactor for a reaction after being heated to 324° C. by the high temperature dehydration reaction gas through an ethanol superheater 103. A high-temperature reaction gas from a third reactor 107 enters a first gas-liquid separation tank 110 after its heat is recovered by the ethanol superheater 103, the ethanol evaporator 108 and the ethanol preheater 101 in sequence. A separated liquid phase therefrom is fed into an evaporation tower 119 by a separation tank discharge pump 111, and a gas phase is fed into a quenching tower 113 after being cooled.

After a gas phase of the first gas-liquid separation tank, a gas phase of a degassing tank and gas exhausted from the drying towers enter the quenching tower 113, an overhead gas of the quenching tower enters a second gas-liquid separation tank 123 after being heated by the tower bottoms of the evaporation tower through a quenching tower overhead gas heater 120. The tower bottoms of the quenching tower are fed into an evaporation tower feed preheater 117 to be heated to 110° C. by the tower bottoms of the evaporation tower, and then enter the evaporation tower 119. Steam produced from the top of the evaporation tower returns to a dehydration reaction section as diluted steam. After heat of the tower bottoms in the evaporation tower are recovered by the evaporation tower feed preheater 117 and the quenching tower overhead gas heater 120, the tower bottoms enter a process water tank 122 after being cooled by an evaporation tower bottom cooler 121.

A gas exhausted from the second gas-liquid separation tank 123 enters the alkaline washing tower 126 after being compressed and cooled, and a gas exhausted from the top of the tower enters a third gas-liquid separation tank 129 after being cooled to 18° C. by low-temperature products of ethylene through a crude ethylene cooler 128. A gas phase separated from the third gas-liquid separation tank 129 is fed into the drying towers to be dehydrated, and the dried ethylene after dehydration is fed into a demethanizing tower 145 and a purification tower 149 to be refined at low temperature.

Dried crude ethylene from the molecular sieve drying system is fed into an ethylene chiller 144 to be recooled by low-temperature propylene after being cooled to −32° C. by the liquid phase products of ethylene through an ethylene precooler 142, and then enters the demethanizing tower 145 after being cooled to −40° C. The overhead gas of the demethanizing tower is fed into a heating furnace 104 as a fuel gas after being cooled to −68° C. by decompressed circulating ethylene in a demethanizing tower condenser 147 and vaporized in a fuel gas tank 156. Ethylene produced in the tower kettle is fed into the purification tower 149, and the products of ethylene produced from the top of the purification tower enter an ethylene reflux tank 152 after being cooled to −36° C. by the low-temperature propylene through a purification tower condenser 151. A part of products of ethylene, serving as the circulating ethylene, are used as a cold source of a demethanizing tower condenser 147 and a propylene cooler 155, and then are fed into the drying towers to serve as a desorbed gas. The rest products of ethylene are fed into an ethylene buffer tank 153. Part of ethylene in the ethylene buffer tank is fed back to the top of the purification tower as reflux, and after cold energy is recycled from the rest of ethylene through the ethylene precooler 142 and the crude ethylene cooler 128, the rest of ethylene is discharged out of the boundary region as the products of ethylene after being heated to 23° C. by hot propylene through a product ethylene heater 157. A demethanizing tower reboiler 146 and a purification tower reboiler 150 are heated by hot propylene, and resulting propylene condensates are fed into a propylene collection tank 159.

Embodiment 2

Ethanol in a raw material tank area enters an ethanol preheater 101 to be heated to 140° C. by a high temperature dehydration reaction gas, then enters an ethanol evaporation tank 102, and is heated to be evaporated in ethanol evaporators 108, 109. A heating medium in the ethanol evaporator 108 is the high temperature dehydration reaction gas. Ethanol steam evaporated from the ethanol evaporation tank 102 is divided into three streams to be fed into the reactor for a reaction after being heated to 327° C. by the high temperature dehydration reaction gas through an ethanol superheater 103. A high-temperature reaction gas from a third reactor 107 enters a first gas-liquid separation tank 110 after its heat is recovered by the ethanol superheater 103, the ethanol evaporator 108 and the ethanol preheater 101 in sequence. A separated liquid phase therefrom is fed into an evaporation tower 119 by a separation tank discharge pump 111, and a gas phase is fed into a quenching tower 113 after being cooled.

After a gas phase of the first gas-liquid separation tank, a gas phase of a degassing tank and gas exhausted from drying towers enter a quenching tower 113, an overhead gas of the quenching tower enters a second gas-liquid separation tank 123 after being heated by the tower bottoms of the evaporation tower through a quenching tower overhead gas heater 120. The tower bottoms of the quenching tower are fed into an evaporation tower feed preheater 117 to be heated to 114° C. by the tower bottoms of the evaporation tower, and then enter the evaporation tower 119. Steam produced from the top of the evaporation tower returns to a dehydration reaction section as diluted steam. After heat of the tower bottoms in the evaporation tower are recovered by the evaporation tower feed preheater 117 and the quenching tower overhead gas heater 120, the tower bottoms enter a process water tank 122 after being cooled by an evaporation tower bottom cooler 121.

A gas exhausted from a second gas-liquid separation tank 123 enters an alkaline washing tower 126 after being compressed and cooled, and a gas exhausted from the top of the tower enters a third gas-liquid separation tank 129 after being cooled to 22° C. by low-temperature products of ethylene through a crude ethylene cooler 128. A gas phase separated from the third gas-liquid separation tank 129 is fed into the drying towers to be dehydrated, and the dried ethylene after dehydration is fed into a demethanizing tower 145 and a purification tower 149 to be refined at low temperature.

Dried crude ethylene from the molecular sieve drying system is fed into an ethylene chiller 144 to be recooled by low-temperature propylene after being cooled to −28° C. by the liquid phase products of ethylene through an ethylene precooler 142, and then enters a demethanizing tower 145 after being cooled to −35° C. The overhead gas of the demethanizing tower is fed into a heating furnace 104 as a fuel gas after being cooled to −64° C. by decompressed circulating ethylene in a demethanizing tower condenser 147 and vaporized in a fuel gas tank 156. Ethylene produced in the tower kettle is fed into the purification tower 149, and the products of ethylene produced from the top of the purification tower enter an ethylene reflux tank 152 after being cooled to −34° C. by low-temperature propylene through a purification tower condenser 151. A part of products of ethylene, serving as the circulating ethylene, are used as a cold source of the demethanizing tower condenser 147 and a propylene cooler 155, and then are fed into the drying towers to serve as a desorbed gas. The rest products of ethylene are fed into an ethylene buffer tank 153. Part of ethylene in the ethylene buffer tank is fed back to the top of the purification tower as reflux, and after cold energy of the rest of ethylene is recovered by the ethylene precooler 142 and a crude ethylene cooler 128, the rest of ethylene is discharged out of the boundary region as the products of ethylene after being heated to 26° C. by hot propylene through a product ethylene heater 157. A demethanizing tower reboiler 146 and a purification tower reboiler 150 are heated by hot propylene, and resulting propylene condensates are fed into a propylene collection tank 159.

Embodiment 3

Ethanol in a raw material tank area enters an ethanol preheater 101 to be heated to 136° C. by a high temperature dehydration reaction gas, then enters an ethanol evaporation tank 102, and is heated to be evaporated in ethanol evaporators 108 and 109. A heating medium in the ethanol evaporator 108 is the high temperature dehydration reaction gas. Ethanol steam evaporated from the ethanol evaporation tank 102 is divided into three streams to be fed into the reactor for a reaction after being heated to 325° C. by the high temperature dehydration reaction gas through an ethanol superheater 103. A high-temperature reaction gas from a third reactor 107 enters a first gas-liquid separation tank 110 after its heat is recovered by the ethanol superheater 103, the ethanol evaporator 108 and the ethanol preheater 101 in sequence. A separated liquid phase therefrom is fed into an evaporation tower 119 by a separation tank discharge pump 111, and a gas phase is fed into a quenching tower 113 after being cooled.

After a gas phase of the first gas-liquid separation tank, a gas phase of a degassing tank and gas exhausted from drying towers enter the quenching tower 113, an overhead gas of the quenching tower enters a second gas-liquid separation tank 123 after being heated by the tower bottoms of the evaporation tower through a quenching tower overhead gas heater 120. The tower bottoms of the quenching tower are fed into an evaporation tower feed preheater 117 to be heated to 112° C. by the tower bottoms of the evaporation tower, and then enter the evaporation tower 119. Steam produced from the top of the evaporation tower returns to a dehydration reaction section as diluted steam. After heat of the tower bottoms in the evaporation tower are recovered by the evaporation tower feed preheater 117 and the quenching tower overhead gas heater 120, the tower bottoms enter a process water tank 122 after being cooled by an evaporation tower bottom cooler 121.

A gas exhausted from a second gas-liquid separation tank 123 enters an alkaline washing tower 126 after being compressed and cooled, and a gas exhausted from the top of the tower enters a third gas-liquid separation tank 129 after being cooled to 20° C. by low-temperature products of ethylene through a crude ethylene cooler 128. A gas phase separated from the third gas-liquid separation tank 129 is fed into the drying towers to be dehydrated, and the dried ethylene after dehydration is fed into a demethanizing tower 145 and a purification tower 149 to be refined at low temperature.

Dried crude ethylene from the molecular sieve drying system is fed into an ethylene chiller 144 to be recooled by low-temperature propylene after being cooled to −30° C. by the liquid phase products of ethylene through an ethylene precooler 142, and then enters the demethanizing tower 145 after being cooled to −38° C. The overhead gas of the demethanizing tower is fed into a heating furnace 104 as a fuel gas after being cooled to −65° C. by circulating ethylene in a demethanizing tower condenser 147 and vaporized in a fuel gas tank 156. Ethylene produced in the tower kettle is fed into the purification tower 149, and the products of ethylene produced from the top of the purification tower enter an ethylene reflux tank 152 after being cooled to −35° C. by low-temperature propylene through a purification tower condenser 151. A part of products of ethylene, serving as the circulating ethylene, are used as a cold source of the demethanizing tower condenser 147 and a propylene cooler 155, and then are fed into the drying towers to serve as a desorbed gas. The rest products of ethylene are fed into an ethylene buffer tank 153. Part of ethylene in the ethylene buffer tank is fed back to the top of the purification tower as reflux, and after cold energy of the rest of ethylene is recovered by the ethylene precooler 142 and the crude ethylene cooler 128, the rest of ethylene is discharged out of the boundary region as the products of ethylene after being heated to 25° C. by hot propylene through a product ethylene heater 157. A demethanizing tower reboiler 146 and a purification tower reboiler 150 are heated by hot propylene, and resulting propylene condensates are fed into a propylene collection tank 159.

The present disclosure has the beneficial technical effects that, through heat exchange among different materials, heat exchange in the system is disposed rationally to reduce the usage amount of a utility medium in the process of preparing ethylene by ethanol dehydration. On the premise of meeting the separation requirements, the energy consumption is reduced greatly, and the equipment investment and the ethylene production cost are decreased.

Equipment unspecified in the present disclosure is conventional equipment, and it can be achieved by adopting methods and equipment well known to those skilled in the art. Although the present disclosure has been described with reference to the specific embodiments and drawings, the present disclosure is not expected to be limited to the specific form here. On the contrary, the scope of the present disclosure is only limited by the appended claims. In addition, although independent features may be included in different claims, these features may be advantageously combined, and the inclusion in different claims does not mean that the combination of features is not feasible and/or advantageous. References to "first", "second," etc., do not exclude plurals.

The invention claimed is:

1. A thermal coupling method for preparing ethylene by ethanol dehydration, includes an ethanol dehydration reaction system, a quenching compression system, an alkaline washing system, a molecular sieve drying system and an ethylene purification and propylene refrigeration cycle system;

preheating, vaporization and superheating a raw material of ethanol with ethanol dehydration reaction products in the ethanol dehydration reaction system serving as a heat source for; preheating a feed stream of the evaporation tower and heating of an overhead gas of a quenching tower with tower kettle fluid of an evaporation tower in the quenching compression system serving as a heat source;

cooling a crude ethylene with products of ethylene in the alkaline washing system serving as a cold source; preheating circulating ethylene with tower kettle fluid of the evaporation tower in the molecular sieve drying system serving as a heat source;

precooling a dried ethylene with the products of ethylene in the ethylene purification and propylene refrigeration cycle system serving as a cold source; cooling an overhead gas of a demethanizing tower and cooling of propylene with the circulating ethylene serving as a cold source;

cooling an overhead gas of a purification tower and further cooling of the ethylene with low-temperature propylene serving as a cold source for; and heating the tower bottoms of the demethanizing tower, the tower bottoms of the purification tower and the products of ethylene with hot propylene serving as a heat source;

the quenching compression system includes an evaporation tower, an evaporation tower feed preheater, an evaporation tower reboiler, a quenching tower, a quenching tower overhead gas heater, a second gas-liquid separation tank, an evaporation tower bottom cooler and a process water tank;

the tower bottoms of the evaporation tower enter the quenching tower overhead gas heater to heat the overhead gas of the quenching tower, and then the tower bottoms of the evaporation tower are fed into the process water tank, the evaporation tower reboiler condensates are fed into the molecular sieve drying system;

the alkaline washing system includes an alkaline washing tower, the crude ethylene cooler and a third gas-liquid separation tank; the products of ethylene from the ethylene purification and propylene refrigeration cycle system enter the crude ethylene cooler to cool crude ethylene produced in the alkaline washing tower, and then the products of ethylene are fed into a product ethylene heater; and the molecular sieve drying system includes drying towers, a circulating ethylene preheater and a steam condensate flash tank; the evaporation tower reboiler condensates from the quenching compression system enter the circulating ethylene preheater to preheat the circulating ethylene, and the cooled reboiler condensates are fed into the steam condensate flash tank; and dried crude ethylene from the molecular sieve drying system is fed into an ethylene chiller to be recooled by low-temperature propylene after being cooled to −32°C by the liquid phase products of ethylene through an ethylene precooler, and then enters the demethanizing tower after being cooled to −40° C.; the overhead gas of the demethanizing tower is fed into a heating furnace as a fuel gas after being cooled to −68° C. by decompressed circulating ethylene in a demethanizing tower condenser and vaporized in a fuel gas tank; ethylene produced in the tower kettle is fed into the purification tower, and the products of ethylene produced from the top of the purification tower enter an ethylene reflux tank after being cooled to −36° C. by the low-temperature propylene through a purification tower condenser; a part of products of ethylene, serving as the circulating ethylene, are used as a cold source of a demethanizing tower condenser and a propylene cooler, and then are fed into the drying towers to serve as a desorbed gas; the rest products of ethylene are fed into an ethylene buffer tank; part of ethylene in the ethylene buffer tank is fed back to the top of the purification tower as reflux, and after cold energy is recycled from the rest of ethylene through the ethylene precooler and the crude ethylene cooler, the rest of ethylene is discharged out of the boundary region as the products of ethylene after being heated to 23° C. by hot propylene through a product ethylene heater; and a demethanizing tower reboiler and a purification tower reboiler are heated by hot propylene, and resulting propylene condensates are fed into a propylene collection tank;

in the ethanol dehydration reaction system, a tube pass inlet of the ethanol preheater is connected with a raw material tank area; a shell pass inlet of the ethanol preheater is connected with a shell pass outlet of the ethanol evaporator;

a tube pass outlet of the ethanol preheater is connected with an inlet of the ethanol evaporation tank;

a shell pass outlet of the ethanol preheater is connected with an inlet of the first gas-liquid separation tank;

a tube pass inlet of the ethanol evaporator is connected with an outlet in a bottom of the ethanol evaporation tank; a shell pass inlet of the ethanol evaporator is connected with a shell pass outlet of the ethanol superheater;

a tube pass outlet of the ethanol evaporator is connected with an inlet in a right side of the ethanol evaporation tank;

a tube pass inlet of the ethanol superheater is connected with an outlet ata top of the ethanol evaporation tank;

a shell pass inlet of the ethanol superheater is connected with an outlet of the third reactor;

a tube pass outlet of the ethanol superheater is connected with an inlet of the heating furnace;

in the quenching compression system, an outlet of the tower kettle of the evaporation tower is connected with a shell pass inlet of the evaporation tower feed preheater;

an outlet of the tower kettle of the quenching tower is connected with a tube pass inlet of the evaporation tower feed preheater;

a tube pass outlet of the evaporation tower feed preheater is connected with an inlet at a top of the evaporation tower;

a shell pass outlet of the evaporation tower feed preheater is connected with a shell pass inlet of the quenching tower overhead gas heater;

an overhead steam outlet of the quenching tower is connected with a tube pass inlet of the quenching tower overhead gas heater;

a tube pass outlet of the quenching tower overhead gas heater is connected with an inlet of the second gas-liquid separation tank; and a shell pass outlet of the quenching tower overhead gas heater is connected with an inlet of the evaporation tower bottom cooler.

2. The thermal coupling method for preparing ethylene by ethanol dehydration according to claim 1, wherein the ethanol dehydration reaction system includes an ethanol preheater, ethanol evaporators, an ethanol evaporation tank, an ethanol superheater, a first gas-liquid separation tank, a third reactor and a heating furnace;

the ethanol dehydration reaction products enter the ethanol superheater to superheat ethanol steam;

the cooled reaction products enter the ethanol evaporators to vaporize the liquid phase raw material of ethylene, and then the reaction products enter the ethanol preheater to preheat the liquid phase raw material of ethylene;

the ethanol dehydration reaction products cooled repeatedly are fed into the first gas-liquid separation tank; and the tower bottoms of the evaporation tower enter the evaporation tower feed preheater to preheat the feed stream of the evaporation tower.

3. The thermal coupling method for preparing ethylene by ethanol dehydration according to claim 2, wherein the ethylene purification and propylene refrigeration cycle system includes an ethylene precooler, an ethylene chiller, a demethanizing tower, a demethanizing tower condenser, a demethanizing tower reboiler, a purification tower, a purification tower condenser, a purification tower reboiler, an ethylene reflux tank, a propylene cooler, a fuel gas tank, a product ethylene heater, a primary propylene flash tank, a propylene collection tank, and a secondary propylene compressor;

the circulating ethylene enters the demethanizing tower condenser to cool the overhead gas of the demethanizing tower, the heated circulating ethylene is fed into the propylene cooler to cool propylene, and then the circulating ethylene is fed into the molecular sieve drying system;

the products of ethylene enter the ethylene precooler to cool the dried crude ethylene, and the heated products of ethylene are fed into the alkaline washing system, and then discharged out of a boundary region after being heated; the low-temperature propylene enters the purification tower condenser to cool the overhead gas of the purification tower, the heated low-temperature propylene is fed into the ethylene chiller to further cool the ethylene, and then the low-temperature propylene is fed into the primary propylene flash tank; and hot propylene from the outside of the boundary region enters the demethanizing tower reboiler, the purification tower reboiler and the product ethylene heater respectively to heat the tower bottoms of the demethanizing tower, the tower bottoms of the purification tower and the products of ethylene, and the cooled propylene is fed into the propylene collection tank.

4. A device for achieving the thermal coupling method for preparing ethylene by ethanol dehydration according to claim 3, wherein in the alkaline washing system, an overhead steam outlet of the alkaline washing tower is connected with a shell pass inlet of the crude ethylene cooler;

a tube pass outlet of the ethylene precooler is connected with a tube pass inlet of the crude ethylene cooler;

a shell pass outlet of the crude ethylene cooler is connected with an inlet of the third gas-liquid separation tank;

a tube pass outlet of the crude ethylene cooler is connected with a tube pass inlet of the product ethylene heater;

in the molecular sieve drying system, a shell pass inlet of the circulating ethylene preheater is connected with a shell pass outlet of the evaporation tower reboiler;

a tube pass inlet of the circulating ethylene preheater is connected with a tube pass outlet of the propylene cooler;

a tube pass outlet of the circulating ethylene preheater is connected with inlets of the drying towers; and a shell pass outlet of the circulating ethylene preheater is connected with an inlet of the steam condensate flash tank.

* * * * *